(12) United States Patent
Hodgson et al.

(10) Patent No.: US 10,010,381 B2
(45) Date of Patent: Jul. 3, 2018

(54) FLEXIBLE TRACKER SYSTEMS

(71) Applicants: Antony John Hodgson, Vancouver (CA); Mark Joseph Semple, Toronto (CA)

(72) Inventors: Antony John Hodgson, Vancouver (CA); Mark Joseph Semple, Toronto (CA)

(*) Notice: Subject to any disclaimer, the term of this patent is extended or adjusted under 35 U.S.C. 154(b) by 0 days.

(21) Appl. No.: 14/733,928

(22) Filed: Jun. 8, 2015

(65) Prior Publication Data

US 2016/0354153 A1    Dec. 8, 2016

Related U.S. Application Data

(60) Provisional application No. 62/010,110, filed on Jun. 10, 2014.

(51) Int. Cl.
*A61B 90/00* (2016.01)
*A61B 34/20* (2016.01)

(52) U.S. Cl.
CPC ...... *A61B 90/39* (2016.02); *A61B 2034/2055* (2016.02); *A61B 2090/3983* (2016.02); *A61B 2090/3991* (2016.02)

(58) Field of Classification Search
CPC ..................................................... A61B 34/20
See application file for complete search history.

(56) References Cited

U.S. PATENT DOCUMENTS

| 8,386,022 | B2 | 2/2013 | Jutras et al. |
| 8,535,329 | B2 | 9/2013 | Sarin et al. |
| 2004/0068263 | A1* | 4/2004 | Chouinard ............. A61B 90/10 606/86 R |

OTHER PUBLICATIONS

"Computation and Validation of Intra-operative Camera Uncertainty" by A.L. Simpson et al. Conference of the IEEE EMBS. Aug. 23-26, pp. 479-482 (2007).*
West, J.B. et al., "Fiducial Point Placement and the Accuracy of Point-based, Rigid Body Registration", Neurosurg. online, vol. 48, No. 4, pp. 810-817, Apr. 2001.
Leardini, A. et al., "Accuracy of Computer-Assisted Surgery", Knee Surgery Using Computer Assisted Surgery and Robotics, 2013, pp. 3-20.
Jung, H.-J. et al., "Fractures Associated with Computer-Navigated Total Knee Arthroplasty. A Report of Two Cases", J. Bone Joint Surg. Am., vol. 89, No. 10, pp. 2280-2284, Oct. 2007.
Beldame, P. et al., "Pin track induced fractures around computer-assisted TKA", Orthop. Traumatal. Surg. Res., vol. 96, No. 3, pp. 249-255, May 2010.

* cited by examiner

*Primary Examiner* — Tse Chen
*Assistant Examiner* — Jason Ip
(74) *Attorney, Agent, or Firm* — Oyen Wiggs Green & Mutala LLP

(57) ABSTRACT

An apparatus and method for tracking the position of one or more connected rigid bodies using markers attached to the rigid bodies by laterally compliant connectors. Systems based on this method are comprised of laterally compliant connectors, a position tracking system and a data processing algorithm to determine the positions and orientations of the rigid bodies. Variations in the methods of attachment of the laterally compliant connectors, the means by which lateral compliance in the connector is produced, and in the layout of the markers are presented.

12 Claims, 10 Drawing Sheets

Fig. 2A
Fig. 2B
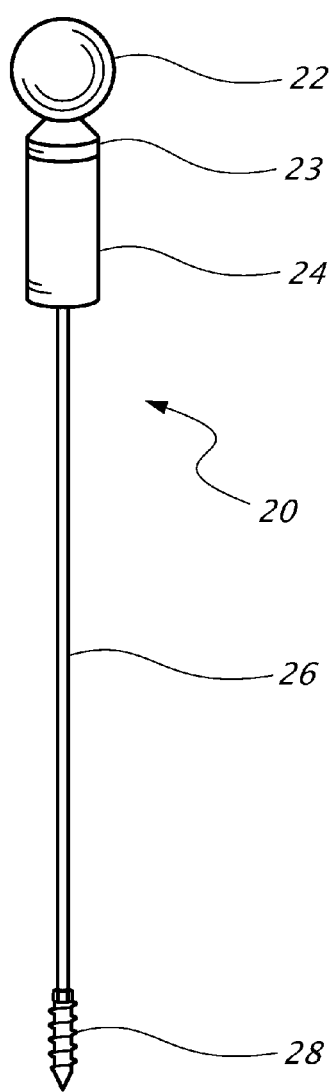
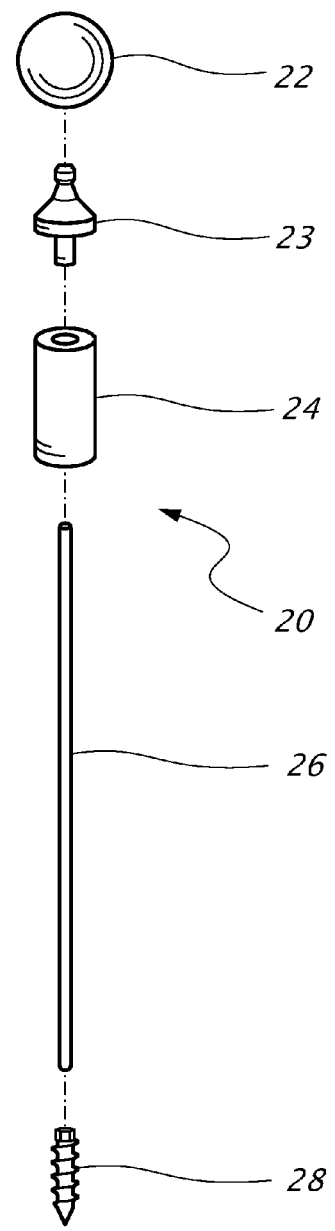

FLEXIBLE TRACKER SYSTEMS

CROSS-REFERENCE TO RELATED APPLICATIONS

This application claims priority from U.S. Provisional Application No. 62/010,110, filed Jun. 10, 2014, which is incorporated by reference.

BACKGROUND OF THE INVENTION

Field of Invention

The present invention relates to the field of computer assisted surgery (CAS), in particular, to procedures in which rigid anatomical structures such as bones are tracked by various sensing systems including, but not limited to, optical, ultrasonic and electromagnetic systems.

Background of Invention

To track the position and orientation (hereafter referred to as the "pose") of a rigid body, such as a tool, bone, or implant, it is sufficient to know the coordinates of three non-collinear points on that body. Most modern tracker systems using optical or ultrasonic sensing means are based on this three-point principle (for examples, see U.S. Pat. No. 8,535,329 B2, U.S. Pat. No. 8,386,022 B2) (alternative approaches such as electromagnetic tracking systems are based on different sensing principles such as detecting the strength of electromagnetic signals generated in coils of different orientations that are mounted in a small device attached to the body being tracked). A tracker based on the three-point principle (hereafter referred to simply as a 'tracker') is typically designed as a rigid structure that is attached to the tracked object and becomes an extension of the tracked body. Current trackers feature three (or more) elements known as markers arranged in some configuration on their proximal end (defined as the end away from the body being tracked) [1]. The principal distinguishing characteristic between different commercially-available trackers is the design and configuration of the markers [2].

The markers are the elements of the system that can be detected by a sensor. In optical systems, the markers are typically detected by some form of camera system, while in ultrasonic systems the markers are detected by some kind of microphone. There are various types of markers used for different systems, generally classified as either passive or active. The difference between the two types of markers is that active markers emit a signal to the sensor, whereas passive markers reflect or echo a signal emitted by the sensor. Both types of markers accomplish the same goal of generating a signal that can be measured by a detector. Note that some systems invert this relationship, placing the detector elements on the body being tracked and the emitting or reflecting elements in the surrounding environment. A practitioner skilled in the art will recognize that such variations in design are well-known.

As mentioned above, the marker coordinates themselves can be measured in several different ways—the most common is to use infrared (IR) stereophotogrammetric sensors (optical tracking), but electromagnetic trackers, ultrasonic emitters and radio-frequency identification (RFID) based trackers can also be used, amongst other techniques. Any technology that can track a number of points or markers in 3D space could be used for this application. At this point in time, optical systems predominate in practice.

However, existing optical trackers have a number of limitations. Since the angular accuracy of the measurement is determined by the ratio of the accuracy limits in measuring the spatial locations of the markers to the distance between the markers, the markers often have to be separated by comparatively large distances to satisfy angular accuracy requirements. The tracker must also be stiff enough to ensure sufficiently low mechanical deformation since the tracking software normally assumes that there is a rigid transformation between the marker array and the body. If there is an inadvertent displacement of the tracker with respect to the bone (e.g., from being knocked out of place during use), the assumption of rigid connection will be violated, which can result in significant errors that can be difficult or impossible to detect [3]. Although rare, there have been reports of long-bone fractures resulting from the insertion of navigation trackers [4], [5]; these fractures may be in part attributable to the relatively large pin diameters needed to ensure rigid fixation (typical systems require that at least two fixation pins be used and that they be engaged bicortically—that is to say, engaged across both cortices or sides of the bone, which makes them relatively intrusive). Due to their size, current trackers are also unsuitable for use with smaller bones, such as the patella or the scaphoid. Therefore there is a need for a tracker system that addresses these limitations.

The foregoing examples of the related art and limitations related thereto are intended to be illustrative and not exclusive. Other limitations of the related art will become apparent to those of skill in the art upon a reading of the specification and a study of the drawings.

OBJECTS AND ADVANTAGES

The principal object of this invention is to provide a tracking system that is less obtrusive, less invasive, and less susceptible to being inadvertently and undetectably displaced and potentially smaller than conventional trackers.

The primary intended field of use of this invention is computer assisted orthopedic surgery, although the tracker system may be adapted for use in fields such as gait analysis. While the primary anticipated sensing modality would be optical in nature, the invention may be readily adapted for use with other sensing modalities by someone skilled in the art.

The invention has several aspects. These aspects may be applied in combination but also have application individually and in sub-combinations.

One aspect of the invention is a set of laterally compliant tracker pins or connectors, which are intended to be anchored into at least one bone or other rigid object to be tracked. A marker is mounted to the tip of each tracker and the spatial location of this marker may be sensed using a position sensing device or system. Because the pins are not required to be rigidly attached to the bone, the diameter of the pins inserted into the bone may be reduced and they may be designed such that only unicortical engagement is used.

A second aspect of the invention is the use of a tracking system to measure the location of the markers attached to the laterally compliant pins. Any of a number of well-known and commercially available tracking systems could potentially be used to address this function.

A third aspect of the invention is a data processing algorithm that determines the pose of the underlying bone, by analyzing the measured location of the markers while accounting for the flexibility of the tracker pins.

The laterally compliant tracker pins and the data processing software may be integrated into a larger system providing additional capabilities, such as navigation systems for surgical procedures.

Variations on the first aspect of the invention include alternative anchoring mechanisms to secure the pins to bones or other objects, as well as variants on the pin design. Pins may have multiple markers attached to the end (e.g., one, two, or three), or markers that report more than just position coordinates (e.g. electromagnetic sensors that can measure orientation information in addition to position information) may be used.

Variations on the third aspect of the invention include alternative formulations of the data processing algorithm. In a preferred embodiment, the data processing algorithm would be based on an observer framework (e.g., the Unscented Kalman Filter), but alternative approaches exist. For example, one could frame the position estimation problem as an instant-by-instant optimization problem. Alternative formulations will be apparent to one skilled in the art.

An extension of the invention would be to use laterally compliant pins in conjunction with a data processing algorithm to measure the pose of a set of rigid bodies that are attached to one another through various kinds of kinematic constraints such as hinges or ball and socket joints that allow for some relative movement between adjacent bodies in the set. In these situations, the number of pins used could be reduced by taking advantage of knowledge of the additional kinematic constraints connecting adjacent rigid bodies.

The invention includes, without limitation, the aspects claimed in the appended claims. The invention also includes all other aspects that may be made the subject of additional claims that may be properly presented in future as supported by the present specifications, drawings and claims.

SUMMARY

Broadly the present invention relates to a system for determining the pose of one or more connected rigid bodies using a plurality of trackable markers attached to the said rigid bodies through zero or more rigid connectors and one or more laterally compliant connectors. Said system additionally comprises a tracking system for measuring the position and optionally orientation of said markers and a data processing system for estimating the pose of said rigid bodies based on the measurements of the said markers reported by the said tracking system.

Preferably, said data processing system is based on an observer framework such as the Unscented Kalman Filter.

Preferably, for the purpose of minimizing the number of said connections to said rigid bodies, a plurality of said markers is attached to said connectors.

Broadly the present invention also relates to a method of determining the pose of one or more connected rigid bodies, comprising the steps of:

(a) Attaching to the said rigid bodies one or more laterally compliant connectors and zero or more rigid connectors, to each of which said laterally compliant connectors and said rigid connectors is attached one or more trackable markers.

(b) Using a position tracking system to measure the position and optionally the orientation of said trackable markers.

(c) Using a data processing system to generate an estimate of the pose of the said rigid bodies based on the measurements of the said trackable marker positions generated by the said position tracking system.

DRAWINGS—FIGURES

The accompanying drawings, which are incorporated in and constitute a part of this specification, illustrate the preferred embodiment of the invention. Further features and advantages of the present invention will become apparent from the following detailed description, taken in combination with the appended drawings, in which:

FIG. 2A is an elevated side view of a flexible tracker pin.

FIG. 2B is an exploded view of a flexible tracker pin.

DRAWINGS—REFERENCE NUMERALS

| 20 | laterally compliant tracker pin | 22 | marker |
|---|---|---|---|
| 23 | marker mounting post | 24 | generic rigid adapter |
| 24A | single marker rigid adapter | 24B | transverse double marker rigid adapter |
| 24C | inline double marker rigid adapter | 24D | triple marker rigid adapter |
| 26 | generic laterally compliant shaft | 26A | slender beam flexible shaft |
| 26B | flat ribbon laterally compliant shaft | 26C | proximal end of rigid shaft |
| 26D | distal end of rigid shaft | 27 | laterally compliant segment for rigid shaft |
| 28 | generic anchor | 28A | screw anchor |
| 28B | smooth tapered anchor | 28C | knurled anchor |
| 28D | expanding plug anchor (closed) | 28E | expanding plug anchor (open) |
| 29 | wrench flats | 30 | anchor shoulder |
| 50 | computer display | 52 | central processor (computer) |
| 54 | position sensor | 55 | user (hand) |
| 58 | tracked body or bone | 60 | estimation of body pose |
| 62 | vertebral body | 63 | intervertebral disc |
| 70 | data processing algorithm | 70A | spatial optimization algorithm |
| 70B | unscented Kalman filter algorithm | 80 | relative anchor coordinates |

| | | | |
|---|---|---|---|
| 85 | advance one time interval | 88 | conventional rigid tracker |
| 90 | upper part of articulated rigid body | 91 | lower part of articulated rigid body |
| 92 | hinge | | |

DETAILED DESCRIPTION

The present invention relaxes the conventional restriction that markers need to be held in a rigid spatial relationship to the body being tracked by taking advantage of the fact that laterally compliant connectors are comparatively stiff in the axial direction and so provide constraint in at least that direction. To fully determine the location of a rigid body in space, at least six constraints must be determined according to the known principles of constraint design (see, for example, Blanding D L, "Exact Constraint", ASME Press, 1999 for details). Accordingly, it is in principle possible to determine and track the pose of a rigid body by tracking the locations of six markers attached to that body through laterally compliant connectors.

As long as the principles of proper constraint are adhered to (e.g., no more than three intersecting lines of constraint, no more than three coplanar constraints, etc., as are well known in the art—again, see Blanding for details), the number of laterally compliant connectors required can be reduced below six by attaching a plurality of markers to each connector. In practice, configurations involving pairs of markers on each of three laterally compliant connectors are practically useful and can be considered a preferred embodiment. The following example embodiments are therefore presented as illustrative but not limiting, and practitioners skilled in the art will be able to conceive of additional configurations not enumerated herein.

Figure 1A:
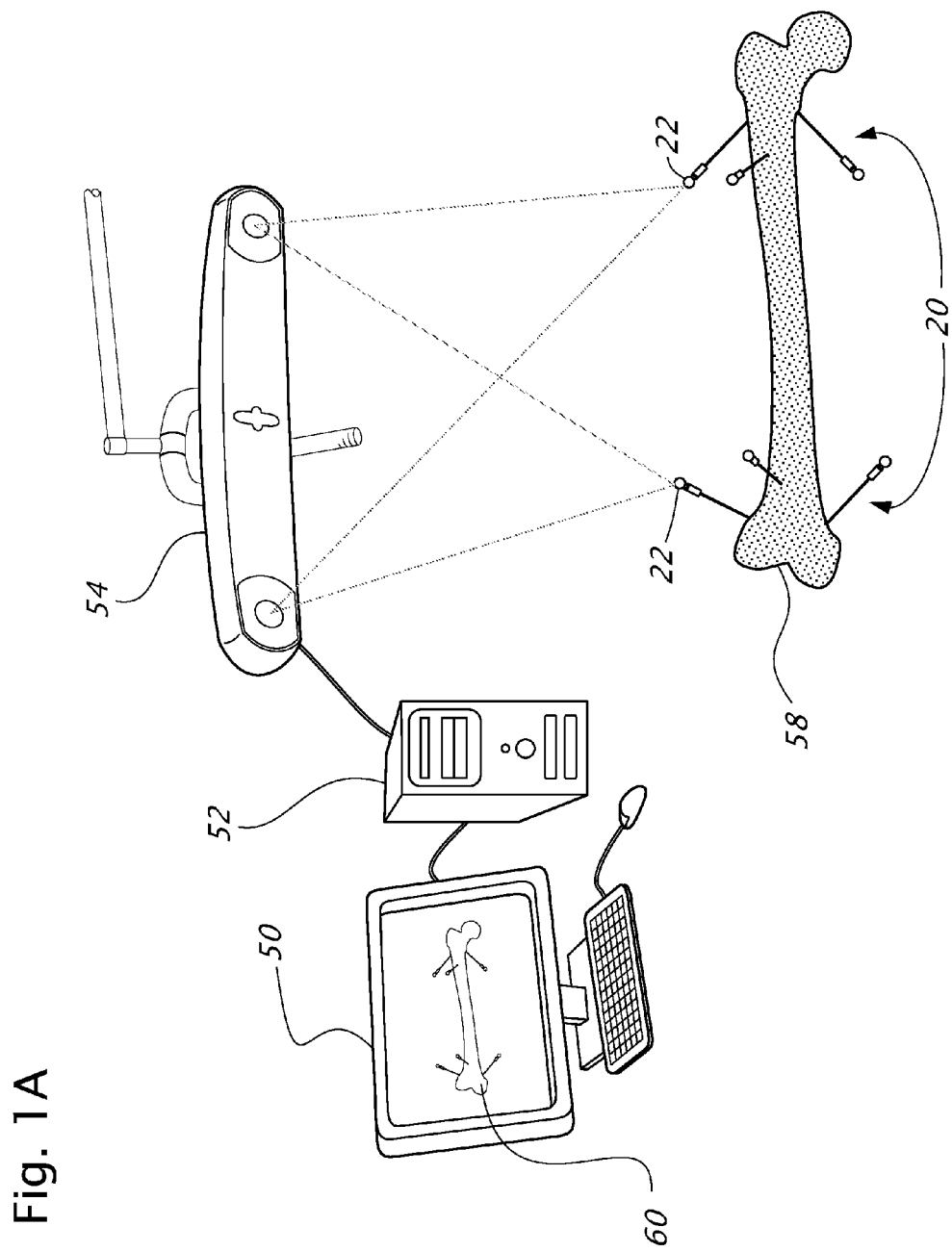
FIG. 1A shows a perspective view of a CAS system that has been modified to incorporate flexible tracker pins.

Illustrative Description of CAS System Components as Shown in FIG. 1A

FIG. 1A illustrates the components of a CAS system that has been modified to incorporate laterally compliant tracker pins. In this scene a set of six laterally compliant tracker pins 20 are anchored into a bone 58. An optical position sensor 54 detects the three-dimensional coordinates of the markers 22 situated on the proximal ends of the laterally compliant tracker pins 20. The sensor 54 is connected to the central processing computer 52. The computer 52 is also connected to a monitor and interface 50 to display the estimation of the bone pose 60.

Figure 1B:
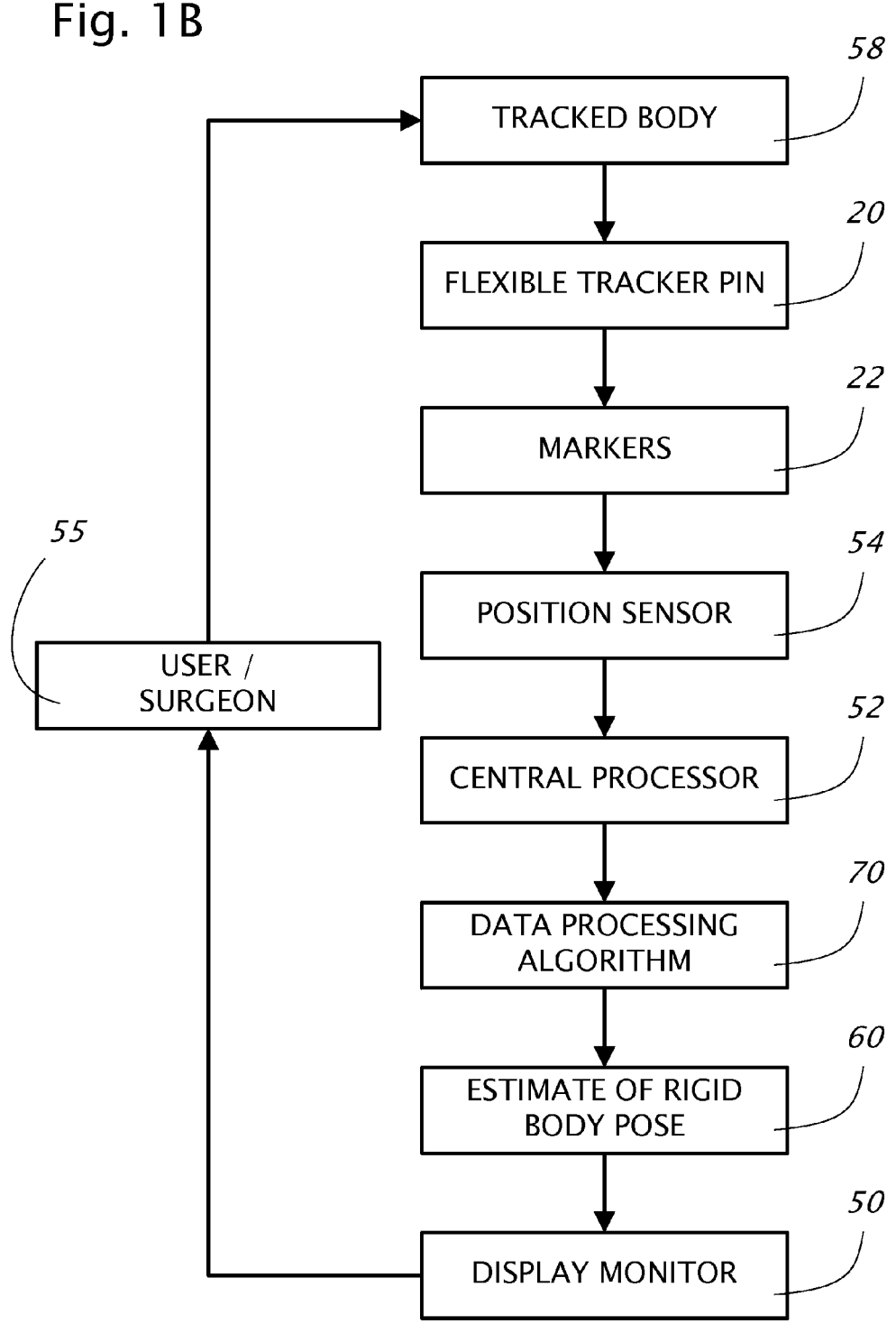
FIG. 1B shows a schematic block diagram of the entire CAS feedback loop that is illustrated in FIG. 1A.

Schematic Description of CAS System Feedback as Shown in FIG. 1B

FIG. 1B shows a schematic block diagram conveying the relationship between components of a CAS system and the associated flow of information. One or more flexible pins 20 are anchored into the tracked body 58 (for example, a bone). The positions of the markers 22 are measured by a position sensor 54, and are transmitted to a central processor 52. A data processing algorithm 70 computes an estimation of the tracked body pose 60. The pose estimation 60 is then displayed on a computer monitor 50 enabling the user (e.g., an orthopaedic surgeon) 55 to base subsequent manipulations of the tracked body 58 on the present estimated position of the tracked body.

Description of One Laterally Compliant Tracker Pin Embodiment 20, as Shown in FIGS. 2A-2B FIGS. 2A and 2B show one embodiment of a laterally compliant tracker pin 20 that has components intended to allow the flexible tracker pin to be attached to the tracked body and to allow the marker to be displaced substantially laterally relative to the axis of the laterally compliant tracker pin. FIG. 2A shows the assembled flexible tracker pin 20, and FIG. 2B shows an exploded view of the same laterally compliant tracker pin 20. In both Figs. a marker 22 snaps onto a mounting post 23 which can be threaded into a hole in a rigid adapter segment 24. The rigid adapter component 24 is welded onto the proximal end of a laterally compliant shaft 26. The distal end of the laterally compliant shaft 26 is welded to an anchor component 28. A number of variations of the laterally compliant tracker pin components are presented in FIGS. 4, 5, and 6.

Figure 3:
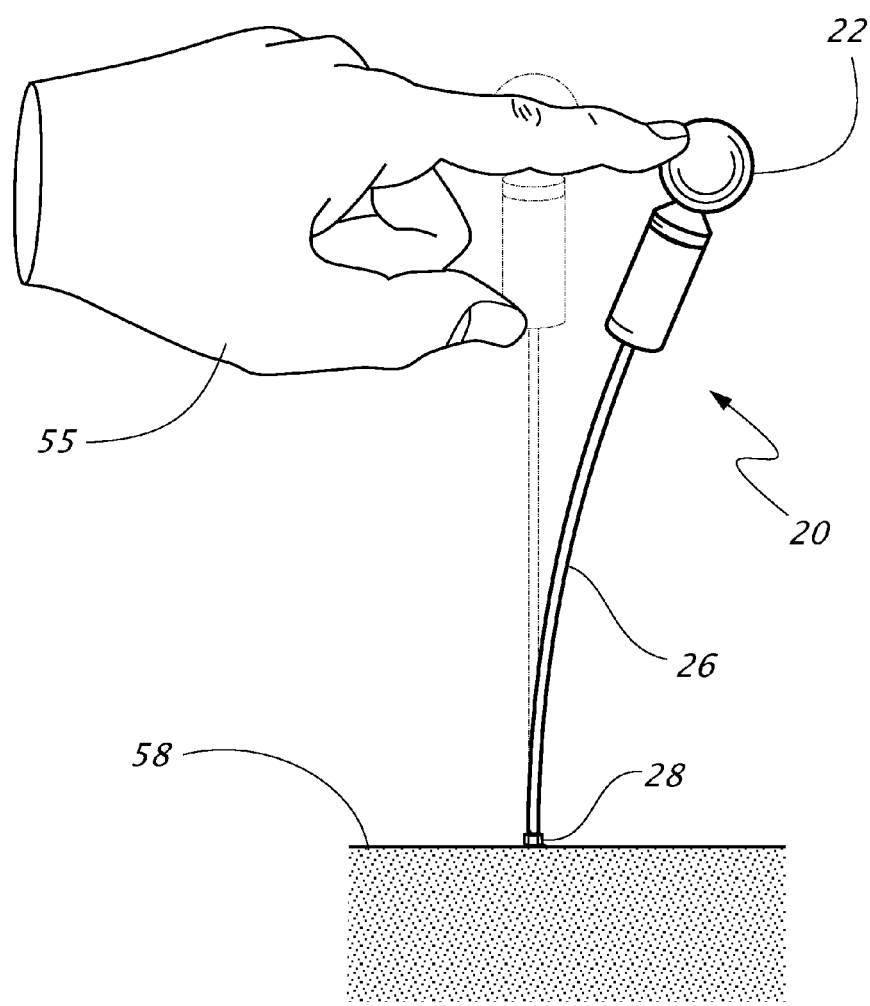
FIG. 3 is a perspective view depicting the flexibility of a flexible tracker pin under external loading.

Physical Deflection of a Laterally Compliant Tracker Pin 20, as Shown in FIG. 3

FIG. 3 depicts a laterally compliant tracker pin 20 being deflected from its original axis by a user's hand 55 while being anchored to a tracked body or bone 58.

The shaft of the tracking pin may be considered laterally compliant (flexible) when the ratio of lateral stiffness to axial stiffness, R, is substantially less than 1. As R is proportional to $(r/L)^2$, where r is the shaft radius and L is the shaft length, one can define a somewhat arbitrary cut-off for flexibility as the point when L is at least five times longer than r. This is based on a specification that the axial stiffness be 100 times larger than the lateral stiffness. One skilled in the art can see that one may chose a tracking pin shaft with a higher or lower ratio for a specific embodiment of the tracking pin as there is no specific value applicable to all applications at which the tracking pin could be considered to be flexible rather than rigid. Flexibility may also be considered to be present if the tip of the pin deflects significantly (on the order of 5-50 degrees) under the application of loads that might be anticipated in the intended application.

The shaft of the tracking pin should also normally be rigid enough that the tracking pin does not deflect significantly under its own weight. Defining δ as the lateral deflection of the pin shaft, and assuming that a force related to the weight of the pin is applied laterally at the tip gives:

$$\delta = \frac{4}{3} k_1 \rho g \pi r^2 L^4$$

where $k_1$ is a small constant multiplying the weight of the tracking pin (selected so as to also account for the weight of the marker attached to the pin tip). The upper limit of δ under such a load may be limited to a small multiple of the shaft diameter, that is $\delta < k_2 r$. This upper limit, $k_2 r$, represents the maximum desired deflection under the tracking pin's own weight (including an allowance for the marker weight). One can determine the minimum diameter size for the shaft of the tracking pin that satisfies this requirement as follows:

$$r_{min} = \frac{4}{3} \frac{k_1}{k_2} \frac{\rho g L^4}{E}$$

Description of Alternative Embodiments

Figure 4A:
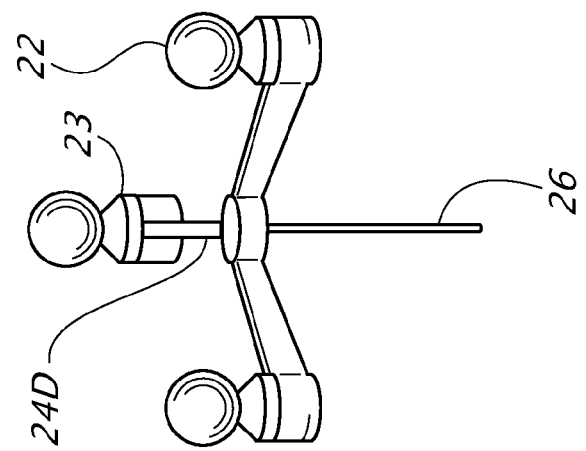
FIGS. 4A-4D show elevated side views of four variations of marker configurations on the proximal end of a laterally compliant tracker pin.
Figure 4B:
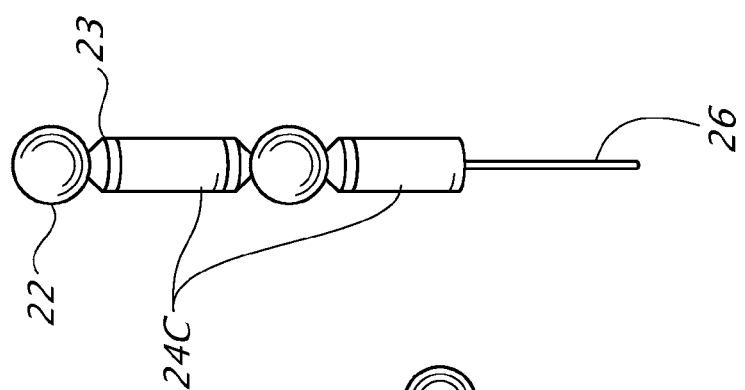
Figure 4C:
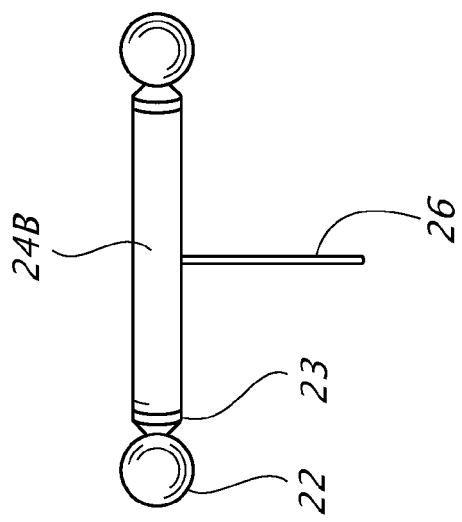
Figure 4D:
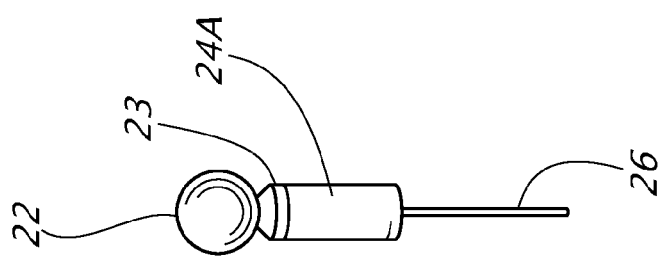

Description of Variations in Proximal Marker Configuration, as Shown in FIGS. 4A-4D In general, the rigid adapter component 24 serves to connect the trackable marker 22 to the proximal end of the laterally compliant shaft 26. Variations of the rigid adapter component 24 enable different configurations of markers atop the laterally compliant shaft 26. Several adapter variations are referenced to as 24A-24D, and are depicted in FIGS. 4A-4D. FIG. 4A shows a single marker adapter 24A, which can position one marker 22 at the end of the laterally compliant shaft 26. FIG. 4B shows a transverse double marker adapter 24B, which holds two markers 22 spread transversely from the laterally compliant shaft 26. FIG. 4C depicts an in-line double marker adapter 24C, which holds the two markers 22 aligned with the laterally compliant shaft 26. FIG. 4D shows a triple marker adapter 24D which connects a cluster of three markers 22 to the proximal end of the laterally compliant shaft 26. These variations are not intended to be exhaustive; alternative embodiments involving more markers and different spatial configurations may be advantageous in particular applications.

Figure 5A:
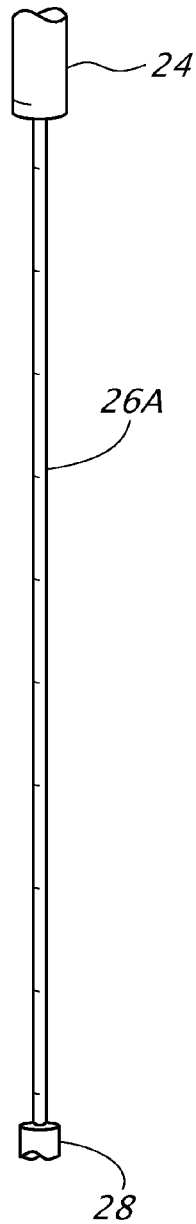
FIGS. 5A-5C show elevated side views of three variations of laterally compliant shaft components.
Figure 5B:
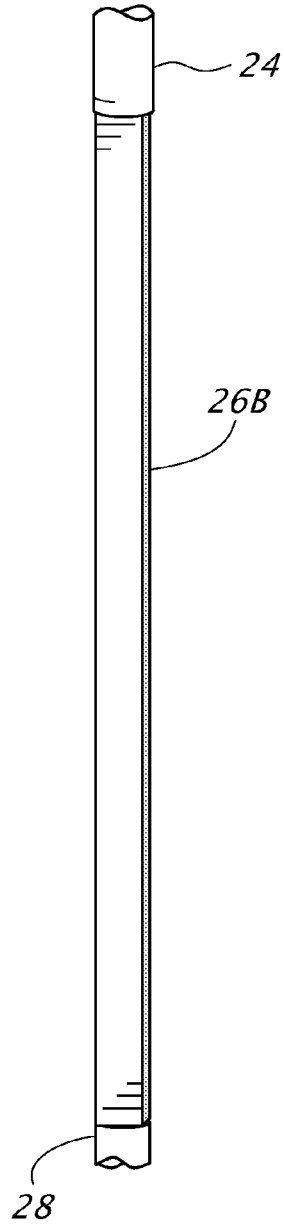
Figure 5C:
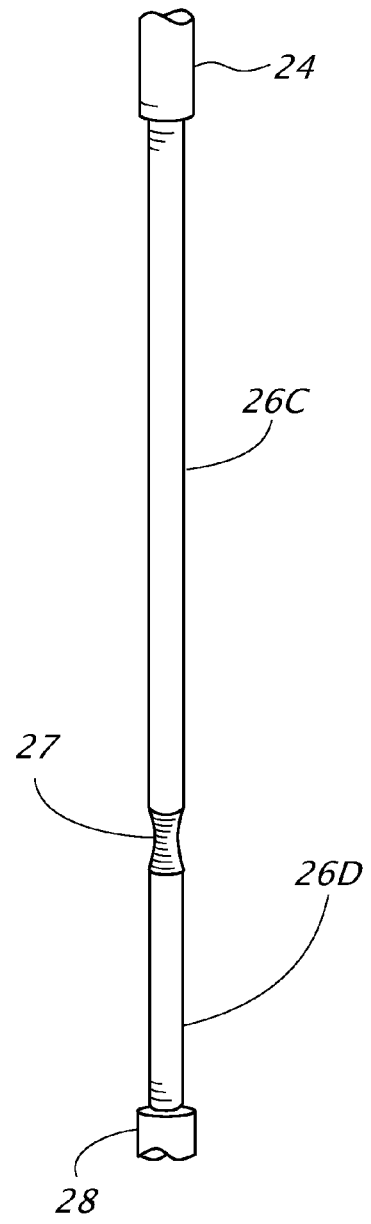

Description of Variations in Flexure Segments, as Shown in FIGS. 5A-5C

Relative motion between the tracked body 58 and the marker 22 is achieved with a laterally compliant shaft or laterally compliant stalk 26. FIGS. 5A-5C show variations in laterally compliant shaft embodiments. FIG. 5A shows a slender, uniform, cylindrical beam 26A which is fixed to an anchor 28 at its distal end, and fixed to a rigid adapter 24 at its proximal end. This laterally compliant shaft 26A allows for lateral deviation of the marker 22 with respect to the tracked body 58 in at least two orthogonal directions. FIG. 5B shows an alternative embodiment of the laterally compliant shaft, which is flat and ribbon-like 26B. This design allows for lateral deviations of the marker 22 in a single direction only. FIG. 5C shows a shaft design in which a distal rigid segment 26D is connected to a proximal rigid segment 26C by a relatively shorter flexible segment 27. This type of shaft design allows deviations similar to the configuration shown in FIG. 5A, but with the zone of flexibility more tightly constrained.

Description of Variations in Anchor Components, Shown in FIGS. 6A-6E

Figure 6E:
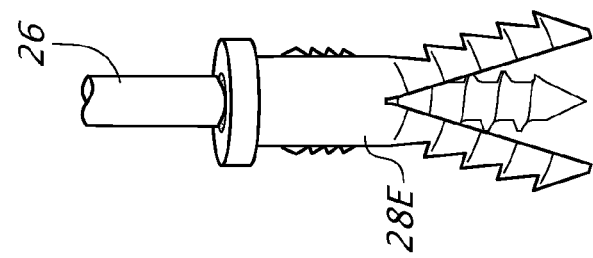
FIGS. 6A-6E show perspective views of four variations of bone attachment anchor components.
Figure 6D:
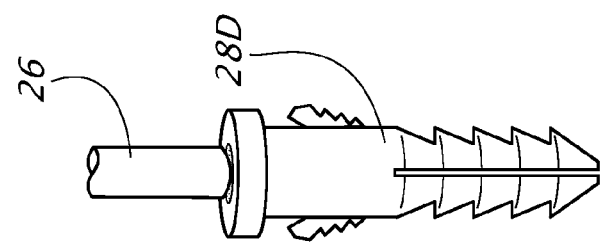
Figure 6C:
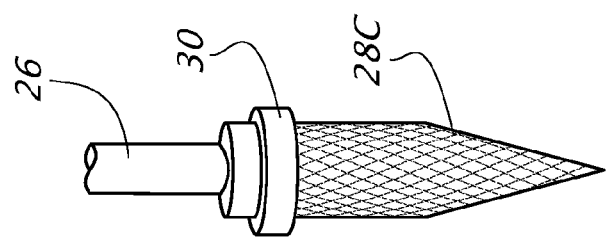
Figure 6B:
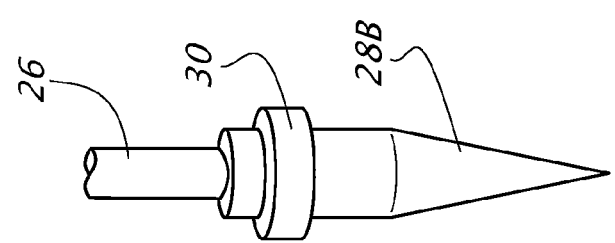
Figure 6A:
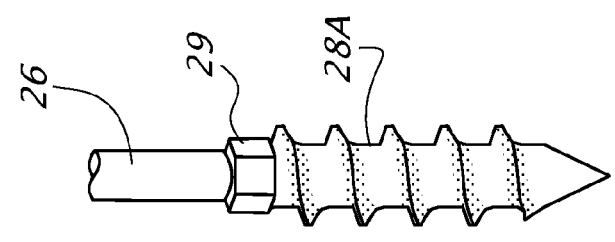

FIGS. 6A-6E show alternative embodiments of the anchor component 28. The generic anchor component 28 serves the purpose of rigidly attaching the distal end of the flexible tracker pin assembly 20 to the tracked body 58. FIG. 6A depicts a screw-type anchor design 28A attached to the distal end of a flexible shaft 26. A segment of wrench flats 29 is cut into the top of the threaded segment 28A to allow for a torqued insertion into a tracked body or bone. FIG. 6B shows a smooth tapered anchor design 28B attached to the distal end of a laterally compliant shaft 26. A ridged shoulder 30 prevents over-insertion of the smooth tapered anchor 28B. FIG. 6C shows a tapered knurled anchor design 28C attached to the distal end of a laterally compliant shaft 26. The knurled anchor 28C is very similar in shape to the smooth tapered anchor 28B, but with a textured finish intended to resist loosening from its anchored position on the tracked body or bone. FIG. 6D shows an expanding-plug anchor design 28D, which, once tapped into the tracked body, can be expanded into its open position 28E, whereupon it could lock into place much like a dry-wall plug, which would be known to one skilled in the art. The embodiments shown here are intended to be illustrative of the key function of providing anchoring between the flexible portion of the laterally compliant tracker pin 20 and the tracked body 58.

Figure 7A:
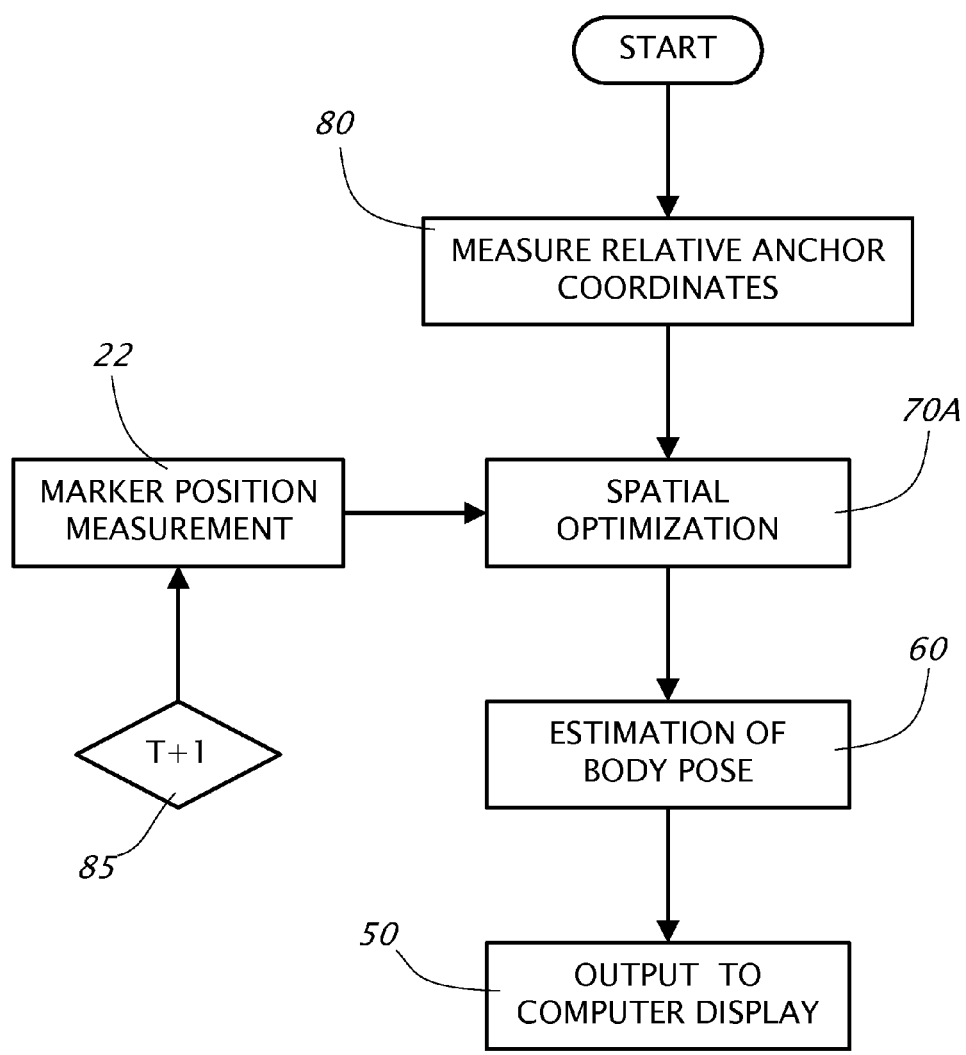
FIG. 7A shows a block diagram for an optimization data processing algorithm.

Description of an Optimization Data Processing Algorithm, Shown in FIG. 7A

FIG. 7A shows a block diagram for one embodiment of a data processing algorithm. After the system has been activated but prior to data processing, the system requires an estimate or measurement of the relative anchor coordinates 80 for each of the laterally compliant tracker pins 20. The relative anchor coordinates 80 will remain constant provided no loosening of the tracker pins occurs during use, and therefore their positions need only be estimated or measured once at the beginning of the procedure. After the relative anchor coordinates 80 have been recorded, a spatial optimization algorithm 70A can compute estimations of tracked body pose 60 given a complete set of marker position measurements from the position sensor 54. The objective function used in the spatial optimization algorithm 70A could express a measure of deviation between the measured marker coordinates and the set of possible marker locations given by the currently-estimated position of the tracked body. A typical objective function for use with a set of six single-marker laterally compliant tracker pins might express the sum of squared distances between the marker coordinates and a spherical surface centred on the anchor coordinates of each corresponding pin with a radius equal to the non-deflected distance between the marker centre and the anchor point. The body pose estimation 60 can then be displayed on the computer monitor 50. More sophisticated versions of the objective function may account for deviations from sphericity due to bending of the pin.

Figure 7B:
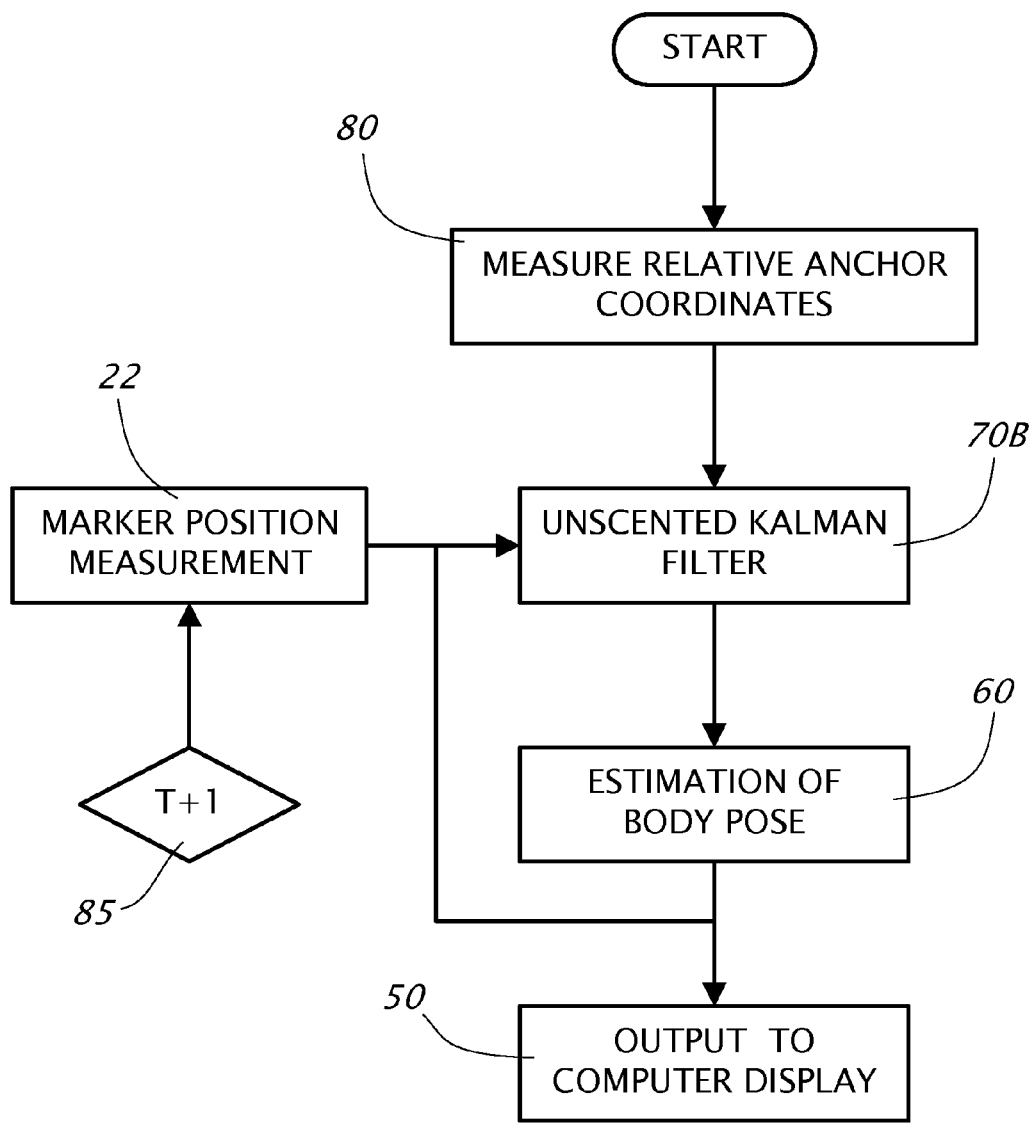
FIG. 7B shows a block diagram for an observer-based data processing algorithm.

Description of the Unscented Kalman Filter Algorithm, Shown in FIG. 7B

FIG. 7B shows a block diagram for a preferred embodiment of a data processing algorithm using an observer-based approach well known in the art known as an Unscented Kalman Filter (UKF) 70B.

The UKF is a state estimator algorithm designed for fusing information from multiple sensors in real time. It recursively updates a previous system state estimate given a potentially noisy state model and new measurement information. The UKF state vector contains spatial information describing the rigid body, and the current pin bending behavior. The state vector includes a minimum of six spatial descriptors of the rigid body (to represent the position and attitude of the rigid body), as well as descriptors of each of the pins' individual angular deflections. The process model is that the body remains static (as any external disturbances are unpredictable)—that is to say: from one instant to the next, we have no a priori information about the bone's motion, so our pre-measurement expectation is that the position and orientation of the bone does not change. The process model can therefore be set to be $f(x)=x$. As such, any bone translations and orientations may be modelled as noise to this "process" of remaining still. The algorithm could also be enhanced, if desired, by adding additional states to represent the linear and angular velocities of the rigid body.

After the system has been activated but prior to data processing, the system requires an estimate or measurement of the relative anchor coordinates 80 of the flexible tracker pins 20. The relative anchor coordinates 80 will remain constant provided no loosening of the tracker pins occurs during use, and therefore their positions need only be estimated or measured once at the beginning of the procedure. After the relative anchor coordinates 80 have been recorded, a UKF algorithm 70B can compute estimations of tracked body pose 60 given a complete set of marker position measurements from the position sensor 54. The UKF is a recursive non-linear system state estimator, meaning that it bases a current estimation of the system state (ie. body pose) on an optimal combination of new information (ie. a new set of marker position coordinates) and past information (ie. the previous system state estimation). The system state comprises variables describing the pose of the tracked body, augmented by variables describing the deflection status of each laterally compliant tracker pin. The UKF algorithm 70B explicitly estimates the deflection status of each laterally compliant tracker pin as a part of its system state. The body pose estimation 60 can then be displayed on the computer monitor 50.

Figure 8:
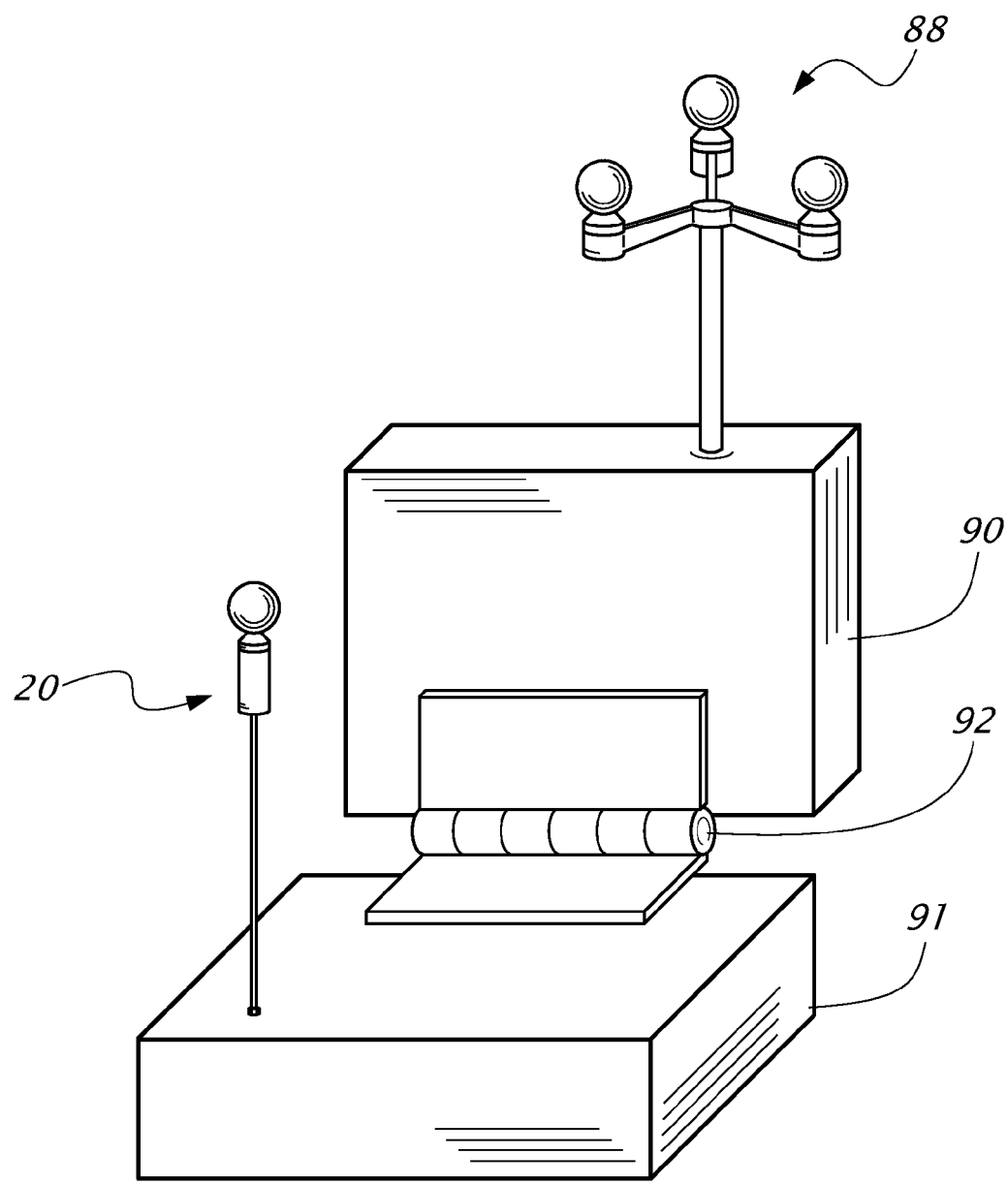
FIG. 8 shows a perspective view of an articulated body being tracked with a rigid tracker and a laterally compliant tracker.

Description of Tracking Articulated Rigid Bodies, as Shown in FIG. 8

FIG. 8 shows a perspective view of an articulated body being tracked. In this example a conventional rigid tracker 88 is attached to one rigid body 90. The rigid tracker 88 fully constrains the pose for this rigid body. Alternatively, some combination of flexible and rigid markers may be used to determine the pose of this rigid body. A hinge 92 joins the first rigid body 90 with a second rigid body 91. The hinge 92 is a one degree of freedom joint, and thus the combined number of degrees of freedom of the articulated system comprised of rigid bodies 90 and 91 and the connecting hinge 92 is seven. The conventional rigid tracker 88 provides six spatial constraints on the first rigid body 90, and therefore only one additional constraint is required to determine the pose of the second rigid body 91. The single laterally compliant tracker pin 20 provides the necessary constraint. The optimization algorithm or the equations used with an observer-based algorithm would be appropriately updated to reflect the behaviour of the hinge 92, using techniques well known to one skilled in the art.

CONCLUSION, RAMIFICATIONS, AND SCOPE

The various embodiments of the invention described above illustrate various situations in which the invention offers advantages over the state of the art rigid tracking systems, as summarized below:

By allowing for flexibility, the attachment between the connectors and the rigid bodies being tracked can be markedly smaller and less intrusive. In an orthopaedic surgical context, the attachments can be unicortical rather than bicortical and can be used on smaller bones that are currently not amenable to being treated using conventional tracking systems. Furthermore, laterally compliant connectors are robust to accidental contact and are far less likely to be accidentally dislodged.

By relaxing the restriction that the markers attached to a single rigid body do not have to be in a rigid relationship to one another, it is possible to distribute the connectors more broadly. In an orthopaedic surgical context, this could enable improved angular resolution and accuracy during measurement.

While a number of exemplary aspects and embodiments have been discussed above, those of skill in the art will recognize that certain modifications, permutations, additions and sub-combinations thereof may be desirable in particular applications. It is therefore intended that the following appended claims and claims hereafter introduced are interpreted to include all such modifications, permutations, additions and sub-combinations.

In particular, various combinations of rigid and flexible connectors may be considered for particular applications, and the invention is not intended to be limited to those forms presented herein as illustrations of the fundamental underlying inventive concept.

REFERENCES

[1] J. B. West, J. M. Fitzpatrick, S. A. Toms, C. R. Maurer, R. J. Maciunas, West, and W. J B, "Fiducial Point Placement and the Accuracy of Point-based, Rigid Body Registration," *Neurosurg. online*, vol. 48, no. 4, p. 810, April 2001.

[2] S. Jutras, L. Amiot, and B. Pelletier, "Multifaceted tracker device for computer-assisted surgery," 2006. U.S. Pat. No. 8,386,022 B2.

[3] A. Leardini, C. Belvedere, A. Ensini, V. Dedda, and S. Giannini, "Accuracy of Computer Assisted Surgery," in Knee Surgery using Computer Assisted Surgery and Robotics, 2013, pp. 3-20.

[4] H.-J. Jung, Y.-B. Jung, K.-S. Song, S.-J. Park, and J.-S. Lee, "Fractures associated with computer-navigated total knee arthroplasty. A report of two cases," *J Bone Joint Surg. Am.*, vol. 89, no. 10, pp. 2280-4, October 2007.

[5] J. Beldame, P. Boisrenoult, and P. Beaufils, "Pin track induced fractures around computer-assisted TKA," *Orthop. Traumatol. Surg. Res.*, vol. 96, no. 3, pp. 249-55, May 2010.

We claim:

1. A system for measuring the pose in space of one or more connected rigid bodies, said system comprising:
   one or more laterally compliant connectors, each of said laterally compliant connectors comprising:
   i. a proximal portion comprising at least one marker;
   ii. an intermediate portion providing substantial lateral compliance in at least one direction; and
   iii. a distal portion comprising an attachment element for attaching the laterally compliant connector to the one or more rigid bodies
   a position tracking system operative to measure the positions in space of a plurality of markers, the plurality of markers including the markers of the one or more laterally compliant connectors
   a data processing system configured to estimate the pose of the one or more rigid bodies based on the measurements of the positions in space of the markers reported by the tracking system and on anchor coordinates of the distal portions of the one or more laterally compliant connectors by performing an optimization using an objective function, the objective function comprising a sum of distances between the positions in space of each of the markers and a corresponding generally spherical surface centered at the corresponding anchor coordinates;
   wherein for each of the laterally compliant connectors the corresponding intermediate portion has a length L that is at least five times greater than a radius r of the intermediate portion.

2. The system as described in claim 1, wherein the one or more laterally compliant connectors comprises at least three laterally compliant connectors, and the one or more laterally compliant connectors collectively comprise six of the markers with no more than three of the six markers being provided by any individual one of the three or more laterally compliant connectors.

3. A method of determining the pose of one or more connected rigid bodies, the method comprising the steps of:
   a. attaching to the said rigid bodies one or more laterally compliant connectors and zero or more rigid connectors, each of the laterally compliant connectors and said rigid connectors supporting one or more trackable markers, b. using a position tracking system to measure the positions of the trackable markers, and c. using a data processing system to generate an estimate of the pose of the rigid bodies based on the measurements of the said trackable marker positions generated by the position tracking system and on anchor coordinates of distal portions of the one or more laterally compliant connectors by performing an optimization using an objective function, the objective function comprising a sum of distances between the positions in space of each of the markers and a corresponding generally spherical surface centered at the corresponding anchor coordinates;

wherein for each of the laterally compliant connectors the corresponding intermediate portion has a length L that is at least five times greater than a radius r of the intermediate portion.

4. The method according to claim 3, comprising using the position tracking system to measure orientations of one or more of the trackable markers.

5. The system according to claim 1, wherein the objective function accounts for deviations from sphericity of the surface.

6. A system for measuring the pose in space of a rigid body, the system comprising:

one or more laterally compliant connectors;

a position tracking system operative to monitor positions in space of six or more markers attached to the body, one or more of the markers attached to the body by each of one or more of the laterally compliant connectors, each of the one or more laterally compliant connectors comprising an anchor attached to the body and a laterally compliant pin supporting each of the corresponding one or more of the markers at a location spaced apart from the anchor such that the one or more markers supported by the laterally compliant connector are movable relative to the body;

a data processing system configured to estimate the pose of the body based on measurements of the positions in space of the six or more markers reported by the tracking system and on a currently-estimated pose of the body by performing an optimization using an objective function, the objective function comprising a measure of deviations between the positions in space of those of the six or more markers attached to the body by the one or more laterally compliant connectors and a set of possible locations of those markers for the currently-estimated pose of the body wherein:

the objective function comprises a sum of distances between the positions in space of each of the six or more markers attached to the body by the one or more laterally compliant connectors and a corresponding generally spherical surface centered at an estimated position of the corresponding one of the anchors; and for each of the laterally compliant connectors the corresponding pin has a length L that is at least five times greater than a radius r of the pin.

7. The system according to claim 6, wherein the data processing system is operative to estimate the pose of the body based on measurements of the positions in space of the six or more markers wherein at least one of the six or more markers is attached to the body by each of three of the laterally compliant connectors.

8. The system according to claim 6, wherein the data processing system is operative to estimate the pose of the body based on measurements of the positions in space of the six or more markers wherein two of the six or more markers are attached to the body by each of three of the laterally compliant connectors.

9. The system according to claim 6, wherein the one or more laterally compliant connectors comprises at least three laterally compliant connectors, and the one or more laterally compliant connectors collectively attach six of the six or more markers to the body with no more than three of the six markers being attached to the body by any individual one of the three or more laterally compliant connectors.

10. The system according to claim 6, comprising a display wherein the data processing system is configured to display on the display the currently-estimated pose of the body.

11. The system according to claim 6, wherein the position tracking system comprises an optical position sensor.

12. The system according to claim 6, wherein the set of possible locations for each of the markers attached to the body by the one or more laterally compliant connectors is defined by a corresponding surface that is fixed relative to an estimated position of the anchor of the corresponding laterally compliant connector.

* * * * *